United States Patent
Hemminger et al.

(10) Patent No.: US 12,296,138 B2
(45) Date of Patent: May 13, 2025

(54) PREFILLED SYRINGE AND METHOD OF PREPARING A PREFILLED SYRINGE

(71) Applicants: F. HOFFMANN-LA ROCHE AG, Basel (CH); GENENTECH, INC., South San Francisco, CA (US)

(72) Inventors: Markus Hemminger, Basel (CH); Ulla Grauschopf, Basel (CH); Frank Bamberg, Basel (CH); Mayumi Bowen, South San Francisco, CA (US); Robert Müller, Basel (CH); Flora Felsovalyi, Basel (CH); Denny Christensen, South San Francisco, CA (US)

(73) Assignees: F. HOFFMANN-LA ROCHE AG, Basel (CH); GENENTECH, INC., South San Francisco, CA (US)

( * ) Notice: Subject to any disclaimer, the term of this patent is extended or adjusted under 35 U.S.C. 154(b) by 492 days.

(21) Appl. No.: 16/651,440

(22) PCT Filed: Sep. 28, 2018

(86) PCT No.: PCT/EP2018/076445
§ 371 (c)(1),
(2) Date: Mar. 27, 2020

(87) PCT Pub. No.: WO2019/063785
PCT Pub. Date: Apr. 4, 2019

(65) Prior Publication Data
US 2020/0297919 A1      Sep. 24, 2020

Related U.S. Application Data

(60) Provisional application No. 62/565,366, filed on Sep. 29, 2017.

(51) Int. Cl.
*A61M 5/00*      (2006.01)
*A61L 2/20*       (2006.01)
(Continued)

(52) U.S. Cl.
CPC ............. *A61M 5/001* (2013.01); *A61L 2/206* (2013.01); *A61L 2/208* (2013.01); *A61M 5/002* (2013.01);
(Continued)

(58) Field of Classification Search
CPC ............................ A61L 2/208; A61M 5/3202
See application file for complete search history.

(56) References Cited

U.S. PATENT DOCUMENTS 5,247,015 A * 9/1993 Bayan ................. B01L 3/50825
                                                                525/98
2005/0075611 A1   4/2005 Hetzler et al.
(Continued)

FOREIGN PATENT DOCUMENTS

EP       3199189 A1 * 8/2017 ........... A61L 31/041
JP    2002-224199 A       8/2002
(Continued)

OTHER PUBLICATIONS

WO 2016068333 A1 Translation.*
WO 2017158805 Translation (Year: 2017).*
International Search Report mailed Dec. 19, 2018 in corresponding International Patent Application No. PCT/EP2018/076445.
(Continued)

*Primary Examiner* — Kevin Joyner
*Assistant Examiner* — Changru Chen
(74) *Attorney, Agent, or Firm* — MEDLER FERRO WOODHOUSE & MILLS PLLC

(57) ABSTRACT

A method of preparing a prefilled syringe is disclosed that includes obtaining a syringe barrel and a needle adaptor cap assembled on the tip of the syringe barrel, wherein the needle adaptor cap has a rubber element tightly sealing the orifice of the tip of the syringe barrel and the syringe barrel
(Continued)

together with the needle adaptor cap assembled on the tip of the syringe barrel is sterilized by a first sterilizing. Filling a drug substance into an interior of the syringe barrel and sealing the interior of the syringe barrel. Packaging the syringe barrel with a rubber stopper sealing the interior thereof and the needle adaptor cap assembled on the tip of the syringe barrel. Providing a second external surface sterilizing of the packaged syringe barrel with the rubber stopper sealing the interior thereof and the needle adaptor cap assembled on the tip of the syringe barrel.

20 Claims, 1 Drawing Sheet

(51) Int. Cl.
*A61M 5/31* (2006.01)
*A61M 5/32* (2006.01)
*B65B 3/00* (2006.01)
*B65B 55/02* (2006.01)

(52) U.S. Cl.
CPC ........ *A61M 5/3137* (2013.01); *A61M 5/3202* (2013.01); *B65B 3/003* (2013.01); *B65B 55/02* (2013.01); *A61L 2202/182* (2013.01); *A61L 2202/24* (2013.01); *A61M 2207/00* (2013.01)

(56) References Cited

U.S. PATENT DOCUMENTS

| | | | | |
|---|---|---|---|---|
| 2013/0280346 A1* | 10/2013 | Powers | ................... | A61L 2/206 |
| | | | | 424/663 |
| 2013/0341206 A1* | 12/2013 | Schenk | ............. | G01N 27/4072 |
| | | | | 205/785.5 |
| 2017/0100543 A1* | 4/2017 | Cabiri | ................ | A61M 5/3213 |

FOREIGN PATENT DOCUMENTS

| | | | | | |
|---|---|---|---|---|---|
| JP | 2007-507308 | A | | 3/2007 | |
| JP | 2015-517860 | A | | 6/2015 | |
| WO | WO-9725075 | A1 | * | 7/1997 | |
| WO | WO-9744068 | A1 | * | 11/1997 | ............... A61L 2/04 |
| WO | WO-0226271 | A1 | * | 4/2002 | |
| WO | 2005/032627 | A1 | | 4/2005 | |
| WO | 2013/178771 | A1 | | 12/2013 | |
| WO | WO-2013184270 | A1 | * | 12/2013 | |
| WO | WO-2015048903 | A1 | * | 4/2015 | |
| WO | WO-2016068333 | A1 | * | 5/2016 | |
| WO | 2016/086299 | A1 | | 6/2016 | |
| WO | 2017/087871 | A1 | | 5/2017 | |
| WO | WO-2017158805 | A1 | * | 9/2017 | ............... A61J 1/14 |

OTHER PUBLICATIONS

Japanese Office action dated Jul. 19, 2022 issued in corresponding Japanese Patent Application No. 2020-517454.

* cited by examiner

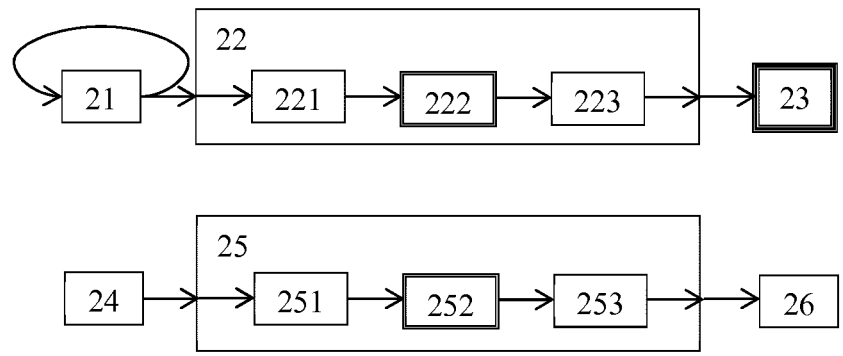
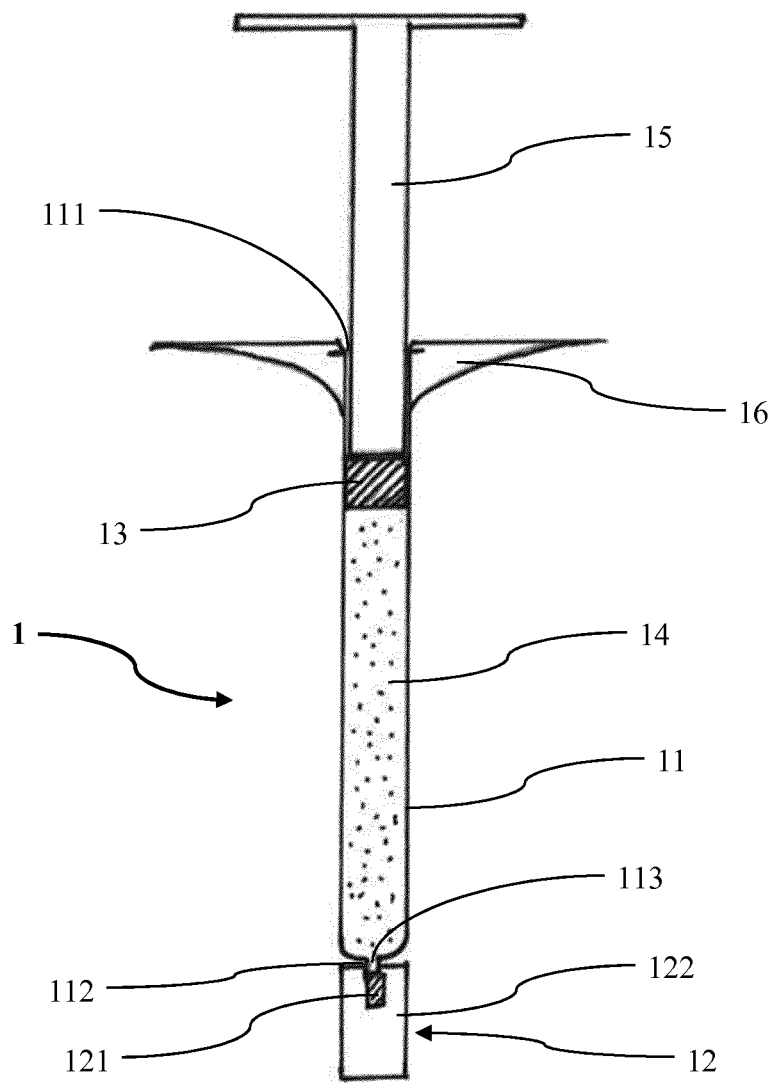
Fig. 2

PREFILLED SYRINGE AND METHOD OF PREPARING A PREFILLED SYRINGE

TECHNICAL FIELD

The present invention relates to a method of preparing a prefilled syringe and more particularly to a prefilled syringe obtained by such a method. Such methods of preparing a prefilled syringe can be used for obtaining a prefilled sterile syringe such that it is suitable to be used for administering pharmaceutical or drug substances such as drug solutions. They can comprise the steps of:

(i) assembling a needle adaptor cap on a tip of a syringe barrel having an open end and the tip with an orifice essentially opposite to the open end;

(ii) first sterilizing the syringe barrel together with the needle adaptor cap assembled on the tip of the syringe barrel, wherein the first sterilizing comprises a main step of exposing the syringe barrel together with the needle adaptor cap assembled on the tip of the syringe barrel to ethylene oxide at predefined conditions;

(iii) filling a drug substance through the open end of the syringe barrel into an interior of the syringe barrel;

(iv) sealing the interior of the syringe barrel by advancing a rubber stopper through the open end of the syringe barrel;

(v) packaging the syringe barrel together with the rubber stopper sealing the interior of the syringe barrel and the needle adaptor cap assembled on the tip of the syringe barrel; and (vi) second external surface sterilizing the external surface of the syringe barrel together with the rubber stopper sealing the interior of the syringe barrel and the needle adaptor cap assembled on the tip of the syringe barrel.

BACKGROUND ART

Many pharmaceutical products (below referred to as drugs or drug products) are processed and/or administered in liquid form wherein injecting the products often is most efficient and preferred. Particularly for subcutaneous, intramuscular, intradermal or intravitreal injection the pharmaceutical substances are often provided in prefilled syringes (PFS) wherein such syringes may have the needles staked-in or be equipped with an adaptor for connecting a needle. In such syringes, the drug is provided in the interior of a barrel of the syringe in a solved or other liquid form ready for being administered. Like this, the user receives a (quasi) ready-to-inject syringe without the requirement to prepare and fill the drug into the syringe, e.g. by transferring the drug from a vial into a disposable syringe. The occurrence of particles and microbiological contaminations injuries and/or inappropriate or inconvenient handling during application can thereby be minimized.

Usually, prefilled syringes comprise a syringe barrel having an open end and a tip with an orifice essentially opposite to the open end, a rubber stopper, a plunger rod, an extended finger flange and a needle adaptor cap with a rubber element. One common possibility for preparation of the PFS involves the following steps:

Assembling the needle adaptor cap on the tip of the syringe barrel wherein the rubber element of the needle adaptor cap tightly seals the orifice of the tip of the syringe barrel.

Sterilizing the assembly of syringe barrel and needle adaptor cap. Thereby, the assembly often is exposed to a sterilizing agent at well-defined conditions, such as sterilant concentration, temperature, duration, relative humidity and/or pressure, allowing a complete sterilization of the assembly even in between the rubber element of the needle adaptor cap and the tip of the syringe barrel. Frequently, ethylene oxide (EO) is used as sterilizing agent.

After this first sterilization, a sterile drug substance is aseptically filled through the open end of the syringe barrel into an interior of the syringe barrel. Such aseptic filling typically is accomplished in cleanrooms in order to maintain sterility. Such cleanrooms are often classified, e.g., by the standards defined as "Sterile Drug Products Produced By Aseptic Processing" or "Manufacture of Sterile Medicinal Products" by Good Manufacturing Practice (GMP) for Active Pharmaceutical Ingredients (API) issued by the International Conference on Harmonisation Regulations. For many parenteral drugs such as ophthalmic drugs for intravitreal injection, the cleanrooms have to conform to the provisions for class A or clean area classification 100 of the GMP standards.

After aseptically filling the drug substance, the interior of the syringe barrel is sealed by advancing the sterile rubber stopper through the open end of the syringe barrel. This step typically is, again, accomplished aseptically in the cleanrooms.

The sealed assembly is then typically moved out of the cleanroom and provided with the plunger rod and eventually with further elements such as, e.g., an extended finger flange and the like. It can further be packaged in a sterile barrier system.

For ophthalmic device combination product, after the PFS being composed and eventually packaged, external surface of the syringe assembly must be sterilized. Thereby, in order to prevent the drug inside the syringe barrel to be affected, it can be important to prevent that the sterilizing agent enters the interior of the syringe barrel. In particular, ingress of the sterilizing agent should be below the limits provided by health authority guidance and the International Organization for Standardization (ISO) requirements, and must not compromise the drug quality until end of shelf life. Thereby, different sterilizing agents may have different limits.

Thus, typically, during preparation of PFS for ophthalmic use two subsequent sterilizations are performed, a first one before filling the drug substance and a second final external surface sterilization once the PFS is completely assembled. Thereby, the aim or extent of sterilization is different in these two sterilizations. In the first complete sterilization, the sterilizing agent is aimed to get through the rubber element and/or through its interface with the tip of the syringe barrel. Therefore, for the first sterilization the rubber element is aimed to have a certain gas permeability for the sterilizing agent. In the second external surface sterilization, however, it is crucial that the rubber element has a comparably low gas permeability for any gas or other substance such that a sterilant gas does not impact a drug quality. Therefore, for the second external surface sterilization the rubber element is aimed to have a minimal gas permeability.

In the light of this challenge or of these counter requirements involved in the first and second sterilizations, there is a need for a method of preparing a prefilled syringe allowing complete and efficient first and second external surface sterilization and for a sterile prefilled syringe having a tightly sealed interior of its syringe barrel.

DISCLOSURE OF THE INVENTION

According to the invention, this need is settled by a method as it is defined by the features of the claims. Preferred embodiments are subject of the dependent claims.

In particular, in one embodiment, the invention is a method of preparing a prefilled syringe (PFS), comprising: (i) obtaining a syringe barrel having an open end and a tip with an orifice essentially opposite to the open end, and a needle adaptor cap assembled on the tip of the syringe barrel, wherein the needle adaptor cap has a rubber element tightly sealing the orifice of the tip of the syringe barrel and the syringe barrel together with the needle adaptor cap assembled on the tip of the syringe barrel is sterilized by a first sterilizing comprising a main step of exposing the syringe barrel together with the needle adaptor cap assembled on the tip of the syringe barrel to ethylene oxide (EO) for about 5 hours (h) to about 60 h at a relative humidity (RH) of about 40% to about 100% and at a temperature of about 30° C. to about 60° C.; (ii) filling a drug substance through the open end of the syringe barrel or through the orifice of the syringe barrel into an interior of the syringe barrel; (iii) sealing the interior of the syringe barrel by advancing a rubber stopper through the open end of the syringe barrel; (iv) packaging the syringe barrel together with the rubber stopper sealing the interior of the syringe barrel and the needle adaptor cap assembled on the tip of the syringe barrel; and (v) second external surface sterilizing the packaged syringe barrel together with the rubber stopper sealing the interior of the syringe barrel and the needle adaptor cap assembled on the tip of the syringe barrel.

The second external surface sterilizing comprises a main step of exposing the packaged syringe barrel together with the rubber stopper sealing the interior of the syringe barrel and the needle adaptor cap assembled on the tip of the syringe barrel to at least 6, i.e. from 6 to about 50 or from 6 to about 20, pulses of vaporized hydrogen peroxide (VHP) for at least 5 minutes (min), or from about 1 min to about 20 min, per pulse at a RH of about 40% to about 100%.

The term "drug" as used herein relates to a therapeutically active agent, also commonly called active pharmaceutical ingredient (API), as well as to a combination of plural such therapeutically active substances. The term also encompasses diagnostic or imaging agents, like for example contrast agents (e.g. MRI contrast agents), tracers (e.g. PET tracers) and hormones, that need to be administered in liquid form to the patient.

The term "drug substance" as used herein relates to a drug as defined above formulated or reconstituted in a form that is suitable for administration to the patient. For example, besides the drug, a drug substance may additionally comprise an excipient and/or other auxiliary ingredients. A particularly preferred drug substance in the context of the invention is a drug solution, in particular a solution for oral administration, injection or infusion.

The term "drug product" as used herein relates to a finished end product comprising a drug substance or a plurality of drug substances. In particular, a drug product may be a ready to use product having the drug substance in an appropriate dosage and/or in an appropriate form for administration. For example, a drug product may include an administration device such as a prefilled syringe or the like.

Preferably, obtaining the syringe barrel and the needle adaptor cap assembled on the on the tip of the syringe barrel comprises: (a) assembling the needle adaptor cap on the tip of the syringe barrel; and (b) first sterilizing the syringe barrel together with the needle adaptor cap assembled on the tip of the syringe barrel, wherein the first sterilizing comprises the main step of exposing the syringe barrel together with the needle adaptor cap assembled on the tip of the syringe barrel to EO for about 5 h to about 60 h at a RH of about 40% to about 100% and at a temperature of about 30° C. to about 60° C.

The initial preparation step (i) above can be performed by the manufacturer of the syringe, which often is different from the manufacturer of the drug substance in the end marketing the PFS. In such situations, the surface-sterilized assembly, e.g. in a blister tray, can be further packaged, e.g. in a carton, and furnished to the drug manufacturer. Alternatively, this step (i) can also be performed by the drug manufacturer himself.

Thus, in another embodiment, the invention is a method of preparing a prefilled syringe, comprising: (i) assembling a needle adaptor cap on a tip of the syringe barrel having an open end and the tip with an orifice essentially opposite to the open end; (ii) first sterilizing the syringe barrel together with the needle adaptor cap assembled on the tip of the syringe barrel, wherein the first sterilizing comprises the main step of exposing the syringe barrel together with the needle adaptor cap assembled on the tip of the syringe barrel to EO preferably for about 5 h to about 60 h preferably at a RH of about 40% to about 100% and preferably at a temperature of about 30° C. to about 60° C.; (iii) filling a drug substance through the open end of the syringe barrel or through the orifice of the syringe barrel into an interior of the syringe barrel; (iv) sealing the interior of the syringe barrel by advancing a rubber stopper through the open end of the syringe barrel; (v) packaging the syringe barrel together with the rubber stopper sealing the interior of the syringe barrel and the needle adaptor cap assembled on the tip of the syringe barrel; and (vi) second external surface sterilizing the packaged syringe barrel together with the rubber stopper sealing the interior of the syringe barrel and the needle adaptor cap assembled on the tip of the syringe barrel, wherein second external surface sterilizing comprises a main step of exposing the packaged syringe barrel together with the rubber stopper sealing the interior of the syringe barrel and the needle adaptor cap assembled on the tip of the syringe barrel to preferably about 6 to about 50, or about 6 to about 20 pulses of VHP for preferably about 1 min to about 20 min per pulse preferably at a RH of about 40% to about 100%.

In the following, effects and preferred features of both embodiments of the method for preparing a prefilled syringe illustrated above are described.

For allowing an efficient second external surface sterilizing, the packaging can be VHP and eventually also EO gas permeable. Such packaging allows for protecting and easy handling of the syringe.

In order to allow the drug substance to be filled through the orifice while being sealed by the rubber element, the needle adaptor cap and particularly its rubber element can be appropriately embodied. For example, the rubber element can be septum-like formed and the cap can be provided with an access passage for allowing a supplying needle to fill the drug substance through the orifice via the access passage and the rubber element.

The term "sterile" as used herein relates to a maximum contamination rate allowing the syringe or another element to be used in an intended application. For example, it can relate to a state of the PFS conforming with the requirements and guidance according to the Standard ST67 of the American National Standards Institute (ANSI) and the Association for the Advancement of Medical Instrumentation (AAMI), i.e. to ANSI/AAMI ST67. More particularly, sterile can mean to conform with level 6 specified in ANSI/AAMI ST67. Analogously, the term "sterilize" relates to bringing a structure or element such as the PFS in a sterile state.

More particularly, the term "sterile" can be directed to achieving a situation free of any viable organisms. In particular, sterilization can relate to a validated process used to render a product essentially free of viable organisms. In such a sterilization process, the nature of microbiological death of reduction can be described by an exponential function. Therefore, the number of microorganisms which survive a sterilization process can be expressed in terms of probability. While the probability may be reduced to a very low number, it can not be reduced to zero.

The filling of the sterile drug substance and the sealing of the interior of the syringe barrel are typically performed aseptically or in an aseptic environment, The PFS can particularly be an ophthalmic prefilled syringe for intravitreal injection of the drug substance. In such administrations, the requirements as to sterility can be particularly high. Therefore, in such treatments, tight sealing of the syringe barrel often is highly important and the demands to the syringe in terms of sterility are also comparably high.

In accordance with the invention, using EO for the first sterilizing allows for achieving an initial sterilization in which the sterilization agent, i.e. EO, penetrates the rubber element such that the interior of the syringe barrel and areas or spaces in between the rubber element and the syringe barrel are sterilized. At the same time, many rubber formulations suitable for being used in the rubber element as well as in the stopper are less permeable for VHP than for EO. Therefore, by using VHP for the second external surface sterilizing allows for achieving that the sterilizing agent, i.e. VHP, does not or not to an undesired extent penetrate the rubber element and/or the stopper. Like this, an external sterilization can be achieved and at the same time the interior of the syringe barrel and particularly the drug substance filled into is not impaired by the sterilizing agent. Thus, the method according to the invention allows for a complete and efficient first and second external surface sterilization and for efficiently providing a sterile prefilled syringe having a tightly sealed interior of its syringe barrel. Furthermore, using VHP in the second external sterilizing allows for sterilizing at a comparably low temperature such as, e.g., at room or ambient temperature. This can be beneficial for many drugs such as biological or biotechnological drugs.

Preferably, the main step of the first sterilizing is performed in a sterilization chamber. In this connection, the term "sterilization chamber" can relate to chambers allowing for providing conditions appropriate for sterilization. In particular, such chambers may be capable of achieving a pressure different from ambient air, temperatures different from ambient temperatures and a specific RH of any selected agents. Advantageously, such chambers allow for adjusting and changing the conditions of their interiors. By using a sterilization chamber for performing the first sterilization, the conditions can be efficiently and precisely tuned and adjusted to be appropriate.

Preferably, the main step of the first sterilizing comprises exposing the syringe barrel together with the needle adaptor cap assembled on the tip of the syringe barrel to a pressure of about 450 mbar to about 1,000 mbar. Additionally or alternatively, in the main step of the first sterilizing, the EO is provided in a concentration of about 400 milligrams per liter (mg/l) to about 800 mg/l. Such a pressure and/or EO concentration allows for further improving the first sterilizing such that its efficiency can be increased without harming any components of the syringe assembly such as, e.g., the rubber element of the needle adaptor cap.

Preferably, the main step of the first sterilizing comprises flushing the syringe barrel together with the needle adaptor cap assembled on the tip of the syringe barrel with air, nitrogen or a combination thereof at a pressure of about 100 mbar or about 200 mbar to about 800 mbar or about 900 mbar after exposing the syringe barrel together with the needle adaptor cap to EO. Such flushing after EO exposition allows for bringing the syringe barrel and needle adaptor cap assembly in a condition to be removed from the sterilization or similar chamber. In particular, the flushing allows to clean the sterilization chamber and/or the assembly such that the sterilization chamber can be opened without exposing the person opening the chamber to any risk.

The main step of the first sterilizing preferably further comprises exposing the syringe barrel together with the needle adaptor cap assembled on the tip of the syringe barrel to a pressure of about 50 mbar to about 200 mbar. Advantageously, such pressure exposition is performed prior to exposing the assembly to EO. This pre-pressurization can be helpful for preparing the syringe before the actual sterilization.

In one preferred embodiment, the first sterilizing comprises a pre-conditioning step of exposing the syringe barrel together with the needle adaptor cap assembled on the tip of the syringe barrel to EO for about 12 h to about 96 h at a RH of about 40% to about 100% and at a temperature of about 30° C. to about 60° C., wherein the pre-conditioning step of the first sterilizing is executed prior the main step of the first sterilization. This pre-conditioning step of the first sterilizing preferably is performed outside the sterilization chamber. Such pre-conditioning allows for efficiently putting the syringe barrel and needle adaptor cap assembly in place to be efficiently sterilized in the main step of the first sterilizing. In particular, it allows for achieving a comparably well gas-permeability of the rubber element of the needle adaptor cap. By performing this comparably time-consuming step outside the sterilization chamber, the utilization of the chamber can be optimized such that the overall process efficiency can be increased.

In another preferred embodiment the first sterilizing comprises a pre-conditioning step of exposing the syringe barrel together with the needle adaptor cap assembled on the tip of the syringe barrel to EO for about 10 minutes (min) to about 2 h at a RH of about 40% to about 100% and at a temperature of about 30° C. to about 60° C., wherein the pre-conditioning step of the first sterilizing is executed prior the main step of the first sterilization. This pre-conditioning step of the first sterilizing preferably is performed inside the sterilization chamber. Such alternative pre-conditioning also allows for efficiently putting the syringe barrel and needle adaptor cap assembly in place to be efficiently sterilized in the main step of the first sterilization. In particular, it allows achieving a comparably well gas-permeability of the rubber element of the needle adaptor cap. However, by performing this step inside the sterilization chamber, the time required for pre-conditioning can essentially be lowered. This may also allow for increasing the overall process efficiency.

Preferably, the first sterilizing comprises an aeration step of exposing the syringe barrel together with the needle adaptor cap assembled on the tip of the syringe barrel to an air flow for at least about 12 h at a temperature of about 30° C. to about 60° C., wherein the aeration step of the first sterilizing is executed after the main step of the first sterilizing. This step allows removing residuals on the syringe barrel and needling adaptor cap assembly. It can be performed inside or outside the sterilization chamber.

Preferably, the second external surface sterilizing comprises a pre-conditioning step of exposing the syringe barrel together with the rubber stopper sealing the interior of the syringe barrel and the needle adaptor cap assembled on the tip of the syringe barrel to about 1 to about 10 pulses of VHP at a temperature of about 20° C. to about 40° C. or of about 25° C. to about 35° C. or of about 27° C. to about 29° C. Thereby, the pre-conditioning step of the second external surface sterilizing preferably is performed outside the sterilization chamber. It further preferably is performed at various different pressures having a low pressure of about 1 mbar to about 10 mbar and a high pressure of about 100 mbar to about 300 mbar. Such pre-conditioning allows for efficiently putting the PFS in place to be sterilized in the main step of the second external surface sterilization. In particular, it allows for achieving a comparably well gas-permeability of the rubber element of the needle adaptor cap as well as of the rubber stopper. By performing this comparably time-consuming step outside the sterilization chamber, the utilization of the chamber can be optimized such that the overall process efficiency can be increased.

Additionally or alternatively, the pre-conditioning step of the second external surface sterilizing can comprise an air removal step in which the syringe barrel together with the rubber stopper sealing the interior of the syringe barrel and the needle adaptor cap assembled on the tip of the syringe barrel is exposed to 1 to 10 pulses of air, nitrogen or a combination thereof at a temperature in range of about 25° C. to about 40° C. and at a pressure in a range of about 1 mbar to about 10 mbar. Thereby, the pressure advantageously varies from a pressure low in a range of about 1 mbar to about 10 mbar and a pressure high of about 100 mbar to about 300 mbar.

Preferably, the second external surface sterilizing comprises a post-conditioning step for removing VHP. By removing the VHP from the PFS as well as from the packaging the amount of residuals can be reduced. This can increase the safety of the finished and packaged PFS. Also, it can increase the quality of the PFS to be applied. Such post-conditioning can be particularly important when using VHP since it tends to be absorbed by some packaging materials which absorption can be relevant for an operator's and patient's safety. Also, residual VHP could diffuse from packaging onto the outer surface of the rubber element. Particularly, in case a septum is used for filling of the syringe, the needle would have to pierce it potentially leading to VHP contact with the drug since the needle might transfer residual VHP through the septum when piercing it.

Thereby, the post-conditioning step of the second external surface sterilizing preferably is performed outside the sterilization chamber. By performing this comparably time-consuming step outside the sterilization chamber, the utilization of the chamber can be optimized such that the overall process efficiency can be increased.

Further, the post-conditioning step of the second external surface sterilizing preferably comprises exposing the syringe barrel together with the rubber stopper sealing the interior of the syringe barrel and the needle adaptor cap assembled on the tip of the syringe barrel to about 6 to about 20 pulses of steam for about 5 min to about 10 min per pulse at various different RH having a low RH of about 10% to about 20% and a high RH of about 70% to about 100%. The term "steam" as used in this context can relate to water vapor. It can be applied at a temperature of about 20° C. to about 40° C., or at a temperature in a range of about 25° C. to about 35° C., or at a temperature in a range of about 27° C. to about 29° C. By applying steam in such a manner, VHP can efficiently be removed without harming or impairing the packaged PFS.

Preferably, the post-conditioning step of the second external surface sterilizing comprises exposing the syringe barrel together with the rubber stopper sealing the interior of the syringe barrel and the needle adaptor cap assembled on the tip of the syringe barrel to about 3 to about 10 pulses of air, nitrogen or a combination thereof at various different pressures having a low pressure of about 1 mbar to about 10 mbar and a high pressure of about 800 mbar to about 1,000 mbar. By applying such pulses of air, nitrogen or a combination thereof, VHP can also efficiently be removed without harming or impairing the packaged PFS. It can be particularly efficient to apply these pulses after the steam pulses of the post-conditioning.

Preferably, the post-conditioning step comprises flushing the syringe barrel together with the rubber stopper sealing the interior of the syringe barrel and the needle adaptor cap assembled on the tip of the syringe barrel with air for about 10 min to about 1 h at a pressure of about 300 mbar to about 1,000 mbar. Such air flushing can help to further increase the efficiency of removing VHP residuals.

Preferably, filling the drug substance into the interior of the syringe barrel and sealing the interior of the syringe are performed in a cleanroom. In this connection, the term "cleanroom" relates to an environment, typically used in manufacturing, with a comparably low level of environmental pollutants such as dust, airborne microbes, aerosol particles, and chemical vapors. Thereby, a cleanroom can have a controlled level of contamination that is specified by the number of particles per cubic meter at a specified particle size. Typically, such cleanrooms are classified, e.g., by the standards defined as "Sterile Drug Products Produced By Aseptic Processing" or "Manufacture of Sterile Medicinal Products" by Good Manufacturing Practice (GMP) for Active Pharmaceutical Ingredients (API) issued by the International Conference on Harmonisation Regulations. For many drug substances such as ophthalmic drugs to be injected directly into the eye, the cleanrooms have to conform to the provisions for class A of the GMP standards. Drug sterility is maintained by aseptically filling the drug substance into the syringe in a class A or clean area classification 100 cleanroom.

Thereby, the second external surface sterilizing preferably is performed outside the cleanroom. Like this, the time the cleanroom is required can be lowered. Usually, operating a cleanroom involves a comparably high effort and is comparably costly, reducing the time in the process in which the cleanroom is required allows for increasing efficiency.

Preferably, in the main step of the second external surface sterilizing, the packaged syringe barrel together with the rubber stopper sealing the interior of the syringe barrel and the needle adaptor cap assembled on the tip of the syringe barrel is exposed to pulses of vaporized hydrogen peroxide at a temperature in a range of about 20° C. to about 40° C., or at a temperature in a range of about 25° C. to about 25° C., or at a temperature in a range of about 27° C. to about 29° C. Second sterilization at such a temperature, more or less at ambient temperature, can be particularly efficient.

Preferably, after the sealing of the open end of the syringe barrel, an auxiliary component is mounted to the syringe barrel. In this connection, the term "auxiliary component" relates to any part provided to complete the PFS. In particular, such auxiliary component can be any combination of a plunger rod inserted into the open end of the syringe barrel, an extended finger flange attached to the syringe barrel or a dosing device for adjusting a dose to be injected. This step in the process allows the assembled or complete PFS to undergo the second external surface sterilization. Like this, the PFS can be provided ready to use also in applications where overall sterility is crucial such as in ophthalmic applications.

Preferably, the rubber element of the needle cap adaptor and the rubber stopper are made of a rubber material having an oxygen transmission rate at 1 atmosphere of not more than about 971 cubic centimeter per square meter ($cm^3/(m^2 \ast d)$) and day, of not more than about 732 $cm^3/(m^2 \ast d)$, of not more than about 200 $cm^3/(m^2 \ast d)$, of not more than about 150 $cm^3/(m^2 \ast d)$, of not more than about 120 $cm^3/(m^2 \ast d)$, of between about 115 $cm^3/(m^2 \ast d)$ and about 116 $cm^3/(m^2 \ast d)$, of not more than about 110 $cm^3/(m^2 \ast d)$, of not more than about 100 $cm^3/(m^2 \ast d)$, of not more than about 90 $cm^3/(m^2 \ast d)$, of not more than about 80 $cm^3/(m^2 \ast d)$, of not more than about 70 $cm^3/(m^2 \ast d)$, of not more than about 65 $cm^3/(m^2 \ast d)$, of between about 63 $cm^3/(m^2 \ast d)$ and about 64 $cm^3/(m^2 \ast d)$ or of about 63.6 $cm^3/(m^2 \ast d)$. Such rubber materials may be particularly suitable for sealing the syringe barrel wherein the on one hand may be first sterilized by EO and appropriately second external surface sterilized by VHP.

Preferably, the drug substance is provided with an oxidation prevention excipient which advantageously is methionine. With such an excipient it can be achieved that oxidation of the pharmaceutical active ingredient of the drug substance is oxidized in case that VHP ingress into the syringe barrel occurs during second external surface sterilizing. Thus, like this, the quality of the drug substance can efficiently be assured.

Another aspect of the invention relates to a prefilled syringe (PFS) comprising (i) a syringe barrel having an open end and a tip with an orifice essentially opposite to the open end; (ii) a needle adaptor cap assembled on the tip of the syringe barrel, wherein the needle adaptor cap has a rubber element tightly sealing the orifice of the tip of the syringe barrel and the syringe barrel together with the needle adaptor cap assembled on the tip of the syringe barrel; (iii) a drug substance arranged in the interior of the syringe barrel; and (iv) a rubber stopper sealing an interior of the syringe barrel. In particular, the prefilled syringe is prepared by a method as described above. Like this, a PFS can be provided which is advantageous in terms of tightness of the interior of the syringe barrel. In addition, such a syringe can be provided in a very sterile fashion. This allows the PFS to be used for sensitive administration of drugs at sensitive locations. In particular, it allows an ophthalmic drug to be injected directly into an eye. Thus, the PFS can be an ophthalmic PFS and can have a syringe barrel volume of about 1 ml or less, or about 0.5 ml or less.

The rubber element of the needle cap adaptor of the PFS and the rubber stopper of the PFS preferably are made of a rubber material having an oxygen transmission rate at 1 atmosphere of not more than about 971 cubic centimeter per square meter ($cm^3/(m^2 \ast d)$) and day, of not more than about 732 $cm^3/(m^2 \ast d)$, of not more than about 200 $cm^3/(m^2 \ast d)$, of not more than about 150 $cm^3/(m^2 \ast d)$, of not more than about 120 $cm^3/(m^2 \ast d)$, of between about 115 $cm^3/(m^2 \ast d)$ and about 116 $cm^3/(m^2 \ast d)$, of not more than about 110 $cm^3/(m^2 \ast d)$, of not more than about 100 $cm^3/(m^2 \ast d)$, of not more than about 90 $cm^3/(m^2 \ast d)$, of not more than about 80 $cm^3/(m^2 \ast d)$, of not more than about 70 $cm^3/(m^2 \ast d)$, of not more than about 65 $cm^3/(m^2 \ast d)$, of between about 63 $cm^3/(m^2 \ast d)$ and about 64 $cm^3/(m^2 \ast d)$ or of about 63.6 $cm^3/(m^2 \ast d)$.

BRIEF DESCRIPTION OF THE DRAWINGS

The method and prefilled syringe according to the invention are described in more detail herein below by way of exemplary embodiments and with reference to the attached drawings, in which:

FIG. 1 shows a flow chart of an embodiment of a method according to the invention; and FIG. 2 shows a schematic side view of an embodiment of a prefilled syringe according to the invention.

DESCRIPTION OF EMBODIMENTS

In the following description certain terms are used for reasons of convenience and are not intended to limit the invention. The terms "right", "left", "up", "down", "under" and "above" refer to directions in the figures. The terminology comprises the explicitly mentioned terms as well as their derivations and terms with a similar meaning. Also, spatially relative terms, such as "beneath", "below", "lower", "above", "upper", "proximal", "distal", and the like, may be used to describe one element's or feature's relationship to another element or feature as illustrated in the figures. These spatially relative terms are intended to encompass different positions and orientations of the devices in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. The devices may be otherwise oriented (rotated 90 degrees or at other orientations), and the spatially relative descriptors used herein interpreted accordingly. Likewise, descriptions of movement along and around various axes include various special device positions and orientations.

To avoid repetition in the figures and the descriptions of the various aspects and illustrative embodiments, it should be understood that many features are common to many aspects and embodiments. Omission of an aspect from a description or figure does not imply that the aspect is missing from embodiments that incorporate that aspect. Instead, the aspect may have been omitted for clarity and to avoid prolix description. In this context, the following applies to the rest of this description: If, in order to clarify the drawings, a figure contains reference signs which are not explained in the directly associated part of the description, then it is referred to previous or following description sections. Further, for reason of lucidity, if in a drawing not all features of a part are provided with reference signs it is referred to other drawings showing the same part. Like numbers in two or more figures represent the same or similar elements.

FIG. 1 shows an embodiment of a method for preparing a PFS 2 according to the invention. In a first step 21 syringe components are obtained and washed as well as siliconized. The components comprise a syringe barrel having an open end and a tip with an orifice essentially opposite to the open end. They further comprise a needle adaptor cap with a rubber element. The rubber element is made of a rubber material having an oxygen transmission rate at 1 atm of 115.5 $cm^3/(m^2 \ast d)$. In the first step 21, the needle adaptor cap is assembled on the tip of the syringe barrel such that the orifice of the tip is tightly sealed by the rubber element.

In a second step 22 the syringe barrel together with the needle adaptor cap assembled on the tip of the syringe barrel, in the following referred to as assembly, is first sterilized. Thereby, the first sterilizing 22 comprises a pre-conditioning step 221, a main step 222 and an aeration step 223.

In the pre-conditioning step 221 of the first sterilizing 22, the assembly is exposed to EO for about 52 hours at a relative humidity of about 60% and at a temperature of about 48° C. The pre-conditioning step 221 of the first sterilizing 22 is performed in a separate environment.

Then the assembly is transferred into a sterilization chamber for the main step 222 of the first sterilizing 22. There, the assembly is initially exposed to a pressure of about 150 mbar for preparing the assembly and particularly the rubber element of the needle adaptor cap. Then, the assembly is exposed to vaporized EO in a concentration of about 700 mg/l for about 25 hours at a relative humidity of about 90%, at a temperature of about 55° C. and at a pressure of about 900 mbar. Before removing the assembly from the sterilization chamber, it is flushed with a nitrogen-air-combination wherein the pressure is continuously raised and lowered between about 150 mbar and about 850 mbar. Like this, the EO is widely removed from the assembly.

After flushing the assembly, it is taken out of the sterilization chamber and treated in the aeration step 223 of the first sterilizing 22. Thereby, the assembly is exposed to air at a temperature of about 45° C. for about 55 h. In the aeration step 223 essentially all residuals of the first sterilization are removed. With the aeration step 223, the first sterilizing ends.

The assembly is then transferred into a class A cleanroom where in a sterile or aseptic environment a filling step 23 is executed. In the filling step 23, a precise amount of an ophthalmic drug solution is filled into the interior of the syringe barrel via its open end. Once the correct amount of the drug is in the interior of the syringe barrel, it is tightly closed by providing a rubber stopper through the open end of the syringe barrel into its interior. The rubber stopper is made of the same rubber material as the rubber element of the needle adaptor cap which has an oxygen transmission rate at 1 atm of 115.5 $cm^3/(m^2*d)$.

The sealed assembly filled with the drug solution is then removed from the cleanroom. There, in a mounting step 24 a plunger rod is pushed through the open end of the syringe barrel until it contacts the rubber stopper inside the interior of the syringe barrel. Also, the syringe barrel is provided with an extended finger flange and a plunger rod for better handling of the syringe and the prefilled syringe (PFS) is finished. The PFS is then blistered for packaging. The blister packaging material has a comparably high permeability for VHP.

Afterwards, the blister package containing the PFS is second external sterilized 25. The second external sterilization comprises a pre-conditioning step 251, a main step 252 and a post-conditioning step 253. In the pre-conditioning step 251 air is removed by exposing the blister package containing the PFS to two air pulses at a pressure of 4 mbar and a temperature of 28° C. Before the air pulses are provided, the blister package and the PFS are warmed up.

After being pre-conditioned, the PFS is transferred to a sterilization chamber in which the main step 252 of the second external surface sterilizing 25 is executed. Thereby, the blister package containing the PFS is exposed to eight pulses of VHP for 5 min per pulse at a pressure of 4 mbar and at a temperature of 28° C.

For removing the VHP from the blister package containing the PFS after second external surface sterilization, it is exposed to seven steam pulses for 5 minutes per pulse, at a temperature of 28° C. and at varying RH alternating from 15% to 85% in the post-conditioning step 253. In the same step, after provision of the steam pulses, the blister package containing the PFS exposed to four air pulses at a temperature of 28° C. and at varying pressures alternating from 4 mbar to 900 mbar. Again in the same step, after the provision of the air pulses, the blister package containing the PFS is flushed with air for 20 min at a pressure of 500 mbar.

After flushing, the packaged PFS is removed from the sterilization chamber and in a last step 26 the PFS is then stored, sold, delivered and in the end used for administrating the drug solution.

FIG. 2 shows an embodiment of a prefilled syringe (PFS) 1 according to the invention obtained by the method described above in connection with FIG. 1. The PFS 1 comprises a syringe barrel 11, a needle adaptor cap 12, a rubber stopper 13, a liquid ophthalmic drug solution 14, a plunger rod 15 and an extended finger flange 16. The syringe barrel 11 has an open end 111 and a tip 112 with an orifice 113 opposite to the open end 111. The needle adaptor cap 12 has a rigid adaptor shell 122 and an elastic rubber element 121 inside the adaptor shell 122. It is assembled on the tip 112 of the syringe barrel 11 such that the rubber element 121 tightly seals the orifice 113 of the tip 112. In particular, the rubber element 121 is pressed onto the outer or lower end of the orifice 113 by mounting the adaptor shell 122 to the tip 112 such that the orifice 113 is closed and sealed. The adaptor shell 122 protects the rubber element 121 and provides an adaptor structure such as a Luer-Lock structure for mounting a needle to the PFS 1 before administration (not visible in FIG. 2). Even though in FIG. 2 the adaptor shell 122 is schematically represented as a single piece, it is understood that typically it is a two or multi part unit.

The drug solution 14 is arranged in an interior of the syringe barrel 11 which interior is sealed by the rubber stopper 13 advanced through the open end 111 of the syringe barrel 11 into an upper portion of the interior of the syringe barrel 11. Extending through the open end 111 of the syringe barrel lithe plunger rod 15 extends into the interior of the syringe barrel 11 such that the proximal end of the plunger rod 15 is adjacent to the rubber stopper 13. At the open end 111 the extended finger flange 16 is mounted to the syringe barrel 11 for a convenient handling of the PFS 1.

The method according to the invention allows that the rubber stopper 13 and the rubber element 121 of the needle adaptor cap 12 are made of a rubber material having advantageous properties. In particular, the rubber material of the rubber stopper 13 and the rubber element 121 has an oxygen transmission rate at 1 atm of 732 $cm^3/(m^2*d)$ or of 115.5 $cm^3/(m^2*d)$. For example, such rubber material can be the rubber formulation FM 30 comprising a styrene butadiene compound which, e.g., is marketed by Datwyler Pharma Packaging International NV as FM30/0, or the rubber formulation 4023/50 comprising Bromobutyl and synthetic Polysoprene which, e.g., is marketed by Aptar Stelmi as GS 6580.

This description and the accompanying drawings that illustrate aspects and embodiments of the present invention should not be taken as limiting—the claims defining the protected invention. In other words, while the invention has been illustrated and described in detail in the drawings and foregoing description, such illustration and description are to be considered illustrative or exemplary and not restrictive. Various mechanical, compositional, structural, electrical, and operational changes may be made without departing from the spirit and scope of this description and the claims. In some instances, well-known circuits, structures and techniques have not been shown in detail in order not to obscure the invention. Thus, it will be understood that changes and modifications may be made by those of ordinary skill within the scope and spirit of the following claims. In particular, the present invention covers further embodiments with any combination of features from different embodiments described above and below.

The disclosure also covers all further features shown in the Figs. individually although they may not have been described in the afore or following description. Also, single alternatives of the embodiments described in the figures and the description and single alternatives of features thereof can be disclaimed from the subject matter of the invention or from disclosed subject matter. The disclosure comprises subject matter consisting of the features defined in the claims or the exemplary embodiments as well as subject matter comprising said features.

Furthermore, in the claims the word "comprising" does not exclude other elements or steps, and the indefinite article "a" or "an" does not exclude a plurality. A single unit or step may fulfil the functions of several features recited in the claims. The mere fact that certain measures are recited in mutually different dependent claims does not indicate that a combination of these measures cannot be used to advantage. The terms "essentially", "about", "approximately" and the like in connection with an attribute or a value particularly also define exactly the attribute or exactly the value, respectively. The term "about" in the context of a given numerate value or range refers to a value or range that is, e.g., within 20%, within 10%, within 5%, or within 2% of the given value or range. Components described as coupled or connected may be electrically or mechanically directly coupled, or they may be indirectly coupled via one or more intermediate components. Any reference signs in the claims should not be construed as limiting the scope.

The invention claimed is:

1. A method of preparing a prefilled syringe, comprising:
obtaining a syringe barrel having an open end and a tip with an orifice essentially opposite to the open end, and a needle adaptor cap assembled on the tip of the syringe barrel, wherein the needle adaptor cap has a rubber element tightly sealing the orifice of the tip of the syringe barrel and the syringe barrel together with the needle adaptor cap assembled on the tip of the syringe barrel is sterilized, prior to filling or sealing an interior of the syringe barrel, by performing a first sterilizing comprising a main step of exposing to the syringe barrel together with the needle adaptor cap assembled on the tip of the syringe barrel to ethylene oxide;
filling a drug substance through the open end of the syringe barrel or through the orifice of the syringe barrel into an interior of the syringe barrel;
sealing the interior of the syringe barrel by advancing a rubber stopper through the open end of the syringe barrel;
packaging the syringe barrel together with the rubber stopper sealing the interior of the syringe barrel and the needle adaptor cap assembled on the tip of the syringe barrel; and
performing a second external surface sterilizing of the packaged syringe barrel together with the rubber stopper sealing the interior of the syringe barrel and the needle adaptor cap assembled on the tip of the syringe barrel,
wherein the second external surface sterilizing comprises a main step of exposing to pulses of vaporized hydrogen peroxide the packaged syringe barrel together with the rubber stopper sealing the interior of the syringe barrel and the needle adaptor cap assembled on the tip of the syringe barrel to at least six pulses of vaporized hydrogen peroxide for at least about five minutes per pulse at a relative humidity of about 40% to about 100%.

2. The method of claim 1, wherein the main step of the first sterilizing is performed in a sterilization chamber.

3. The method of claim 1, wherein the main step of the first sterilizing comprises exposing the syringe barrel together with the needle adaptor cap assembled on the tip of the syringe barrel to ethylene oxide for about 5 hours to about 60 hours at a relative humidity of about 40% to about 100% and at a temperature of about 30° C. to about 60° C.

4. The method of claim 1, wherein the main step of the first sterilizing comprises exposing the syringe barrel together with the needle adaptor cap assembled on the tip of the syringe barrel to ethylene oxide at a pressure of about 450 millibars to about 1000 millibars.

5. The method of claim 1, wherein in the main step of the first sterilizing the ethylene oxide is provided in a concentration of about 400 milligrams per liter to about 800 milligrams per liter.

6. The method of claim 1, wherein the main step of the first sterilizing comprises flushing the syringe barrel together with the needle adaptor cap assembled on the tip of the syringe barrel with air, nitrogen or a combination thereof at a pressure of about 100 millibars or about 200 millibars to about 800 millibars or about 900 millibars after exposing the syringe barrel together with the needle adaptor cap to ethylene oxide.

7. The method of claim 1, wherein the first sterilizing comprises a pre-conditioning step of exposing the syringe barrel together with the needle adaptor cap assembled on the tip of the syringe barrel to ethylene oxide for about 12 hours to about 96 hours at a relative humidity of about 40% to about 100% and at a temperature of about 30° C. to about 60° C., wherein the pre-conditioning step of the first sterilizing is executed prior the main step of the first sterilization, wherein the pre-conditioning step of the first sterilizing is performed outside a sterilization chamber.

8. The method of claim 1, wherein the first sterilizing comprises a pre-conditioning step of exposing the syringe barrel together with the needle adaptor cap assembled on the tip of the syringe barrel to ethylene oxide for about 10 minutes to about 2 hours at a relative humidity of about 40% to about 100% and at a temperature of about 30° C. to about 60° C., wherein the pre-conditioning step of the first sterilizing is executed prior the main step of the first sterilization, wherein the pre-conditioning step of the first sterilizing preferably is performed inside a sterilization chamber.

9. The method of claim 1, wherein the first sterilizing comprises an aeration step of exposing the syringe barrel together with the needle adaptor cap assembled on the tip of the syringe barrel to an air flow for at least about 12 hours at a temperature of about 30° C. to about 60° C., wherein the aeration step of the first sterilizing is executed after the main step of the first sterilizing.

10. The method of claim 1, wherein the second external surface sterilizing comprises a pre-conditioning step of exposing the packaged syringe barrel together with the rubber stopper sealing the interior of the syringe barrel and the needle adaptor cap assembled on the tip of the syringe barrel to about 1 to about 10 pulses of vaporized hydrogen peroxide at a temperature of about 20° C. to about 40° C. or of about 25° C. to about 35° C. or of about 27° C. to about 29° C., wherein the pre-conditioning step of the second external surface sterilizing is performed outside a sterilization chamber, and the pre-conditioning step of the second external surface sterilizing is performed at various different pressures having a low pressure of about 1 millibar to about 10 millibars and a high pressure of about 100 millibars to about 300 millibars.

11. The method of claim 1, wherein the second external surface sterilizing comprises a post-conditioning step for removing vaporized hydrogen peroxide, wherein the post-conditioning step of the second external surface sterilizing is performed outside a sterilization chamber, wherein the post-conditioning step comprises flushing the packaged syringe barrel together with the rubber stopper sealing the interior of the syringe barrel and the needle adaptor cap assembled on the tip of the syringe barrel with air for about 10 minutes to about 1 hour at a pressure of about 300 millibars to about 1000 millibars.

12. The method of claim 1, wherein filling the drug substance into the interior of the syringe barrel and sealing the interior of the syringe are performed in a cleanroom, wherein the second external surface sterilizing is performed outside the cleanroom.

13. The method of claim 1, wherein, after the sealing of the open end of the syringe barrel, an auxiliary component is mounted to the syringe barrel.

14. The method of claim 1, wherein the rubber element of the needle adaptor cap and the rubber stopper are made of a rubber material having an oxygen transmission rate at 1 atmosphere of not more than about 971 cubic centimeter per square meter and day, of not more than about 732 cubic centimeter per square meter and day, of not more than about 200 cubic centimeter per square meter and day, of not more than about 150 cubic centimeter per square meter and day, of not more than about 120 cubic centimeter per square meter and day, of between about 115 cubic centimeter per square meter and day and about 116 cubic centimeter per square meter and day, of not more than about 110 cubic centimeter per square meter and day, of not more than about 100 cubic centimeter per square meter and day, of not more than about 90 cubic centimeter per square meter and day, of not more than about 80 cubic centimeter per square meter and day, of not more than about 70 cubic centimeter per square meter and day, of not more than about 65 cubic centimeter per square meter and day, of between about 63 cubic centimeter per square meter and day and about 64 cubic centimeter per square meter and day, or of about 63.6 cubic centimeter per square meter and day.

15. The method of claim 1, wherein, in the main step of the second external surface sterilizing, each of the pulses of vaporized hydrogen peroxide is followed by a pulse of air, nitrogen or a combination thereof for about 20 seconds to about 10 minutes per pulse at a pressure in range of about 300 millibars to about 1000 millibars.

16. The method of claim 1, wherein, in the main step of the second external surface sterilizing, each of the pulses of vaporized hydrogen peroxide is followed by a pulse of steam for about 10 seconds to about 5 minutes per pulse at a relative humidity of about 60% to about 100%.

17. The method of claim 1, wherein, in the main step of the second external surface sterilizing, the packaged syringe barrel together with the rubber stopper sealing the interior of the syringe barrel and the needle adaptor cap assembled on the tip of the syringe barrel is exposed to the pulses of vaporized hydrogen peroxide at a temperature in a range of about 20° C. to about 40° C., or at a temperature in a range of about 25° C. to about 35° C., or at a temperature in a range of about 27° C. to about 29° C.

18. The method of claim 1, wherein the drug substance is provided with an oxidation prevention excipient, and wherein the oxidation prevention excipient is methionine.

19. A method of preparing a prefilled syringe, comprising:
obtaining a syringe barrel having an open end and a tip with an orifice essentially opposite to the open end, and a needle adaptor cap assembled on the tip of the syringe barrel, wherein the needle adaptor cap has a rubber element tightly sealing the orifice of the tip of the syringe barrel and the syringe barrel together with the needle adaptor cap assembled on the tip of the syringe barrel is sterilized, prior to filling or sealing an interior of the syringe barrel, by performing a first sterilizing comprising a main step of exposing to the syringe barrel together with the needle adaptor cap assembled on the tip of the syringe barrel to ethylene oxide;
filling a drug substance through the open end of the syringe barrel or through the orifice of the syringe barrel into the interior of the syringe barrel;
sealing the interior of the syringe barrel by advancing a rubber stopper through the open end of the syringe barrel;
packaging the syringe barrel together with the rubber stopper sealing the interior of the syringe barrel and the needle adaptor cap assembled on the tip of the syringe barrel; and
performing a second external surface sterilizing of the packaged syringe barrel together with the rubber stopper sealing the interior of the syringe barrel and the needle adaptor cap assembled on the tip of the syringe barrel,
wherein the second external surface sterilizing comprises a main step of exposing to pulses of vaporized hydrogen peroxide the packaged syringe barrel together with the rubber stopper sealing the interior of the syringe barrel and the needle adaptor cap assembled on the tip of the syringe barrel to pulses of vaporized hydrogen peroxide, and
wherein, in the main step of the second external surface sterilizing, each of the pulses of vaporized hydrogen peroxide is followed by a pulse of air, nitrogen or a combination thereof for about 20 seconds to about 10 minutes per pulse at a pressure in range of about 300 millibars to about 1000 millibars.

20. A method of preparing a prefilled syringe, comprising:
obtaining a syringe barrel having an open end and a tip with an orifice essentially opposite to the open end, and a needle adaptor cap assembled on the tip of the syringe barrel, wherein the needle adaptor cap has a rubber element tightly sealing the orifice of the tip of the syringe barrel and the syringe barrel together with the needle adaptor cap assembled on the tip of the syringe barrel is sterilized, prior to filling or sealing an interior of the syringe barrel, by performing a first sterilizing comprising a main step of exposing to the syringe barrel together with the needle adaptor cap assembled on the tip of the syringe barrel to ethylene oxide;
filling a drug substance through the open end of the syringe barrel or through the orifice of the syringe barrel into the interior of the syringe barrel;
sealing the interior of the syringe barrel by advancing a rubber stopper through the open end of the syringe barrel;
packaging the syringe barrel together with teh rubber stopper sealing the interior of the syringe barrel and the needle adaptor cap assembled on the tip of the syringe barrel; and performing a second external surface sterilizing of the packaged syringe barrel together with the rubber stopper sealing the interior of the syringe barrel and the needle adaptor cap assembled on the tip of the syringe barrel, wherein the second external surface sterilizing comprises a main step of exposing to pulses of vaporized hydrogen peroxide the packaged syringe barrel together with the rubber stopper sealing the interior of the syringe barrel and the needle adaptor cap assembled on the tip of the syringe barrel to pulses of vaporized hydrogen peroxide, and wherein, in the main step of the second external surface sterilizing, each of the pulses of vaporized hydrogen peroxide is followed by a pulse of steam for about 10 seconds to about 5 minutes per pulse at a relative humidity of about 60% to about 100%.

* * * * *